United States Patent
Sostek

(10) Patent No.: US 9,040,921 B2
(45) Date of Patent: May 26, 2015

(54) ANALYTICAL METHODS

(71) Applicant: Harvard Bioscience, Inc., Holliston, MA (US)

(72) Inventor: Ron Sostek, Newton, MA (US)

(73) Assignee: Harvard Apparatus Regenerative Technology, Inc., Holliston, MA (US)

(*) Notice: Subject to any disclaimer, the term of this patent is extended or adjusted under 35 U.S.C. 154(b) by 0 days.

(21) Appl. No.: 13/952,641

(22) Filed: Jul. 28, 2013

(65) Prior Publication Data

US 2014/0124670 A1 May 8, 2014

Related U.S. Application Data

(60) Provisional application No. 61/741,820, filed on Jul. 28, 2012.

(51) Int. Cl.
  *G01J 5/10*  (2006.01)
  *G01J 5/08*  (2006.01)
  *G01J 5/02*  (2006.01)
  *A61L 27/56* (2006.01)
  *G01J 5/00*  (2006.01)

(52) U.S. Cl.
  CPC ............ *G01J 5/10* (2013.01); *G01J 2005/0081* (2013.01); *G01J 5/0871* (2013.01); *G01J 5/025* (2013.01); *G01J 5/0265* (2013.01); *G01J 2005/0077* (2013.01); *A61L 27/56* (2013.01)

(58) Field of Classification Search
  CPC ............................... G01N 21/35; G01B 5/208
  USPC ................... 250/340, 341.1–341.8
  See application file for complete search history.

(56) References Cited

U.S. PATENT DOCUMENTS

| | | | |
|---|---|---|---|
| 4,492,867 A * | 1/1985 | Laarhoven et al. | 250/339.09 |
| 4,541,438 A | 9/1985 | Parker et al. | |
| 5,452,716 A | 9/1995 | Clift | |
| 5,504,331 A * | 4/1996 | Lane et al. | 250/339.09 |
| 5,526,112 A | 6/1996 | Sahagen | |
| 5,666,956 A | 9/1997 | Buchert | |
| 5,841,139 A | 11/1998 | Sostek et al. | |
| 5,865,738 A | 2/1999 | Morcos et al. | |
| 5,919,135 A | 7/1999 | Lemelson | |
| 5,945,674 A * | 8/1999 | Dukor | 250/339.11 |
| 6,277,082 B1 | 8/2001 | Gambale | |
| 6,452,180 B1 * | 9/2002 | Nistler et al. | 250/341.4 |
| 6,515,284 B1 * | 2/2003 | Walle et al. | 250/341.6 |

(Continued)

FOREIGN PATENT DOCUMENTS

WO WO 2011/034627 A2 3/2011
WO WO 2011/062621 A2 5/2011

OTHER PUBLICATIONS

Spring, "Infrared emission spectra of in vivo human skin," Specialia, 1966, pp. 262-264.*

(Continued)

*Primary Examiner* — Kiho Kim
(74) *Attorney, Agent, or Firm* — Wolf, Greenfield & Sacks, P.C.

(57) ABSTRACT

Aspects of the disclosure provide techniques for detecting differences and/or changes in biological and non-biological material using infrared imaging. Aspects of the disclosure are useful for monitoring and evaluating synthetic scaffolds and engineered tissue and organs for tissue engineering and transplantation.

35 Claims, 2 Drawing Sheets

(56) References Cited

U.S. PATENT DOCUMENTS

| | | |
|---|---|---|
| 6,587,701 B1 | 7/2003 | Stranc et al. |
| 6,676,654 B1 | 1/2004 | Balle-Petersen et al. |
| 6,718,189 B2 | 4/2004 | Rohrscheib et al. |
| 6,881,584 B1 | 4/2005 | Lenhard et al. |
| 6,917,039 B2* | 7/2005 | Nicolaides et al. ........ 250/341.1 |
| 6,986,739 B2 | 1/2006 | Warren et al. |
| 7,045,786 B2* | 5/2006 | Mandelis et al. .......... 250/341.1 |
| 7,164,133 B2* | 1/2007 | Hjertman et al. ........ 250/339.11 |
| 7,316,922 B2 | 1/2008 | Streeter |
| 7,534,255 B1 | 5/2009 | Streeter et al. |
| 7,697,976 B2 | 4/2010 | Wu et al. |
| 7,893,410 B2* | 2/2011 | Sykora et al. .............. 250/492.1 |
| 7,963,168 B2* | 6/2011 | Ouchi .............................. 73/643 |
| 8,507,263 B2 | 8/2013 | Asnaghi et al. |
| 2006/0155193 A1 | 7/2006 | Leonardi et al. |
| 2007/0005139 A1* | 1/2007 | Vacanti et al. .............. 623/13.17 |
| 2007/0152157 A1* | 7/2007 | Page ............................. 250/340 |
| 2011/0033918 A1 | 2/2011 | Asnaghi et al. |
| 2013/0030548 A1* | 1/2013 | Ling ................................ 623/23 |
| 2013/0041265 A1 | 2/2013 | Sostek et al. |
| 2013/0177972 A1 | 7/2013 | Green et al. |
| 2014/0107803 A1 | 4/2014 | Grosse |
| 2014/0124670 A1 | 5/2014 | Sostek |
| 2014/0141552 A1 | 5/2014 | Sostek et al. |
| 2014/0377848 A1 | 12/2014 | Zink et al. |
| 2015/0011892 A1 | 1/2015 | Sostek et al. |

OTHER PUBLICATIONS

Chandler, Self-powered sensors: Harvesting electricity from small temperature differences could enable a new generation of electronic devices that don't need batteries. MIT News. Feb. 11, 2010. Part I. Retrieved Jun. 19, 2013 from http://web.mit.edu/newsoffice/2010/energy-harvesting.html. 2 pages.

Demos et al., Investigation of near-infrared autofluorescence imaging for the detection of breast cancer. IEEE J Selected Topics Quantum Electronics. Jul.-Aug. 2005;11(4):791-8.

Gaughan, Thermal imaging is gaining acceptance as a diagnostic tool. Biophotonics International. Nov.-Dec. 1998; pp. 48-53.

Rolfe, Sensing in tissue bioreactors. Meas Sci Technol. 2006 Jan 31;17:578-83.

Kannan et al., The antithrombogenic potential of a polyhedral oligomeric silsesquioxane (POSS) nanocomposite. Biomacromolecules. Jan. 2006;7(1):215-23. Epub Nov. 15, 2005.

Mather et al., Meeting the needs of monitoring in tissue engineering. Regenerative Med. Mar. 2007;2(2):145-160.

Petersen, In vitro development of engineered lung tissue. Department Biomed Engineering Duke Univ. Doctoral Dissertation. 2009. 283 pages.

Teebken et al., Tissue engineering of vascular grafts: human cell seeding of decellularised porcine matrix. Eur J Vasc Endovasc Surg. Apr. 2000;19(4):381-6.

* cited by examiner

ANALYTICAL METHODS

RELATED APPLICATIONS

This Application claims priority under 35 U.S.C. §119(e) to U.S. Provisional Application Ser. No. 61/741,820, entitled "ANALYTICAL METHODS" filed on Jul. 28, 2012, which is herein incorporated by reference in its entirety.

BACKGROUND

The characteristics of biological and non-biological materials are generally evaluated using physical or functional tests to determine or quantify one or more properties. For example, the strength or structural integrity of a material can be evaluated by subjecting it to physical challenges that test its response to stretching, twisting, compressing, heating, cooling, or other physical forces or conditions. For example, the physical properties of a synthetic scaffold material for tissue engineering can be evaluated by determining whether the scaffold is resistant to the type and amplitude of physical forces that it will be exposed to during cellularization and tissue growth in a bioreactor and subsequently after implantation into a recipient (e.g., a human recipient).

Materials can be inspected visually to determine whether they present any obvious visual signs of structural or functional failure. However, visual evaluation often is not sufficient to identify structural or functional deficiencies or to determine the extent to which a material has desired structural or functional properties.

SUMMARY

In some embodiments, aspects of the invention relate to using infrared contrasts to detect and/or evaluate structural or functional characteristics of biological or non-biological material. According to some embodiments, structural variations in a material alter the infrared emissivity of the material. In some embodiments, surface variations (e.g., cracks, folds, different compositions, compressions, abrasions, etc.) can impact the infrared emissivity of the material. In some embodiments, variations beneath the surface of a material also can impact the infrared emissivity of the material. In some embodiments, the type (e.g., wavelength) and strength (e.g., amplitude) of infrared emission variations associated with a particular physical property or function of interest can be determined and validated experimentally (e.g., under controlled conditions, including under particular temperature conditions). An infrared detector then can be adapted (e.g., calibrated or designed) to increase or optimize its sensitivity to the infrared emission changes that are associated with the physical or functional change of interest (e.g., under the controlled conditions), as opposed to calibrating the detector to be sensitive to infrared emissions associated with temperature changes. In some embodiments, the detector is not physically modified, but rather the analysis of the detected infrared emissions is modified to focus on infrared emissions that are associated with the physical or functional properties of interest rather than to focus on infrared emissions that are associated with particular temperature changes.

In some embodiments, a method of detecting a physical or functional property at a first site of an object comprises detecting a first infrared emission from the first site and identifying a contrast between the first infrared emission and a second infrared emission, wherein the contrast is indicative of a physical or functional property. In some embodiments, the object is a biological object. In some embodiments, the object is a non-biological object. In some embodiments, the object is a tissue or organ. In some embodiments, the object is a synthetic scaffold for engineering a tissue or organ. In some embodiments, the natural or engineered tissue or organ is skin, lung, liver, heart, muscle, airway, or kidney. In some embodiments, the tissue or organ is engineered and is evaluated in a bioreactor or after implantation into a subject. In some embodiments, a natural tissue or organ is evaluated in vivo in a subject.

In some embodiments, the first infrared emission is a level or pattern of different levels of infrared emission at the first site (e.g., under defined or controlled conditions). In some embodiments, the second infrared emission is a level or pattern of different levels of infrared emission (e.g., for the same defined or controlled conditions). In some embodiments, the second infrared emission is a reference infrared emission (e.g., level or pattern of different levels) that is indicative of a desired structure or function. In some embodiments, the second infrared emission is a different reference infrared emission (e.g., level or pattern of different levels) that is indicative of a deficient structure or function. It should be appreciated that the reference infrared emission can be obtained from previous assays and can be stored (e.g., in a database) for comparison with subsequent infrared emissions (e.g., obtained experimentally).

In some embodiments, the second infrared emission is an emission detected from a second site on the material of interest. In some embodiments, the second site is in proximity to the first site on the material of interest.

In some embodiments, aspects of the disclosure relate to techniques and devices for monitoring and evaluating synthetic scaffolds and engineered tissues and organs for transplantation into a recipient (e.g., a human host). In some embodiments, aspects of the invention can be used to evaluate a scaffold at one or more stages. For example, in some embodiments, a synthetic scaffold is evaluated during synthesis to determine the presence or absence of surface properties and patterns indicative of an appropriate physical configuration (e.g., relative to a reference infrared signal or pattern). In some embodiments, a synthetic scaffold is evaluated to determine one or more properties of the scaffold. For example, if there are one or more channels or networks of channels for delivering fluids, then the integrity, connectivity, relative permeability, etc., or a combination thereof, can be evaluated using techniques described herein. In some embodiments, a synthetic scaffold is evaluated to determine one or more physical properties of the scaffold, for example, to evaluate torsional and bending properties using infrared signals or patterns (e.g., relative to reference signals or patterns). In some embodiments, a synthetic scaffold is evaluated to confirm an appropriate response to temperature (e.g., to evaluate the effects of different temperatures, for example liquids of different temperatures, on the surface or internal properties of a scaffold). In some embodiments, a synthetic scaffold is evaluated during or after cellularization and/or cell growth or development, for example, to confirm that appropriate or sufficient cellularization occurred (e.g., by comparing infrared signals to known levels or patterns of infrared associated with appropriate cellularization). In some embodiments, a synthetic scaffold is evaluated to confirm that a sufficient connection (e.g., fluid connection that does not leak excessively) is made between one or more conduits of a synthetic scaffold (e.g., a cellularized or non-cellularized scaffold) and a bioreactor. In some embodiments, one or more cannula or other fluid pathways are connected to fluid pathways of a bioreactor (e.g., for liquid or gas delivery to tissue or organs that are growing in the bioreactor).

In some embodiments, methods described herein are used to monitor and/or evaluated cell growth and development in a bioreactor. In some embodiments, methods described herein are used to identify and evaluate levels and patterns of infrared emission that are indicative that an engineered tissue or organ is ready (e.g., has sufficient functional and structural properties) for implantation into a host (e.g., a human tissue or organ recipient). It should be appreciated that one or more of these signatures could be useful by itself. However, in some embodiments, an IR signal or pattern of IR levels can be used to assist in the evaluation of synthetic tissue or organs (e.g., along with other physical or physiological indicia).

In some embodiments, methods described herein are used to evaluate a tissue or organ in a host (e.g., a human host). For example, methods can be used to evaluate appropriate growth and implantation of an engineered tissue or organ (for example by evaluating fluid or gas flow into the tissue or organ or a portion thereof). In some embodiments, the presence of excessive fluid leaks in an implant recipient can be detected. In some embodiments, these can be corrected by additional surgical intervention.

Accordingly, in some embodiments, an infrared level or pattern is detected, displayed and/or analyzed. This information is then used to determine one or more structural or functional properties of interest (e.g., by comparing it to one or more reference signals or patterns). In some embodiments, this can lead to one or more additional steps (e.g., additional synthetic or growth steps, additional surgical intervention). In some embodiments, this can result in material (e.g., a synthetic scaffold) not being used if it does not have appropriate properties or if it has one or more undesirable properties.

These and other aspects are described in more detail below and with reference to the drawings.

DETAILED DESCRIPTION

Figure 1A:
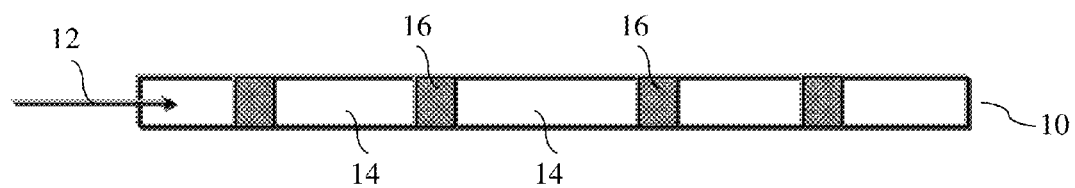
FIG. 1A illustrates a non-limiting embodiment of a side view of a conduit showing zones of fluid or gas that have been introduced into the conduit at different temperatures as seen in infrared imaging.

Aspects of the invention relate to detecting and analyzing infrared emissions to evaluate structural and functional characteristics of biological and non-biological material. In some embodiments, aspects of the invention relate to using natural levels of infrared emission from biological and/or non-biological materials to identify different emissivity levels or emissivity contrasts that can be indicative of structural and/or functional differences (e.g., in the absence of temperature differences). In some embodiments, infrared contrast analysis also can be used to detect and/or analyze temperature differences that can be indicative of structural and/or functional characteristics.

In some embodiments, a contrast in infrared emissivity between two or more different materials, or between two or more different regions of an object or device, can be indicative of different structural and/or functional properties (e.g., associated with different surface structural characteristics and/or sub-surface structural characteristics that affect infrared emissivity of a material, object, or device, and that can be detected using infrared imaging and/or analysis to detect and/or analyze infrared emission levels from the material, object, or device, or one or more regions thereof. In some embodiments, it is the presence of an infrared emissivity contrast, or a pattern of infrared emissivity contrasts that can be used to detect structural features of interest. In some embodiments, a level of infrared emission or a pattern of infrared emissions can be compared to reference levels or patterns e.g., in some embodiments that are indicative of a desired structural or functional characteristic, or in some embodiments that are indicative of an unwanted structural or functional characteristic.

In some embodiments, an infrared emission level or pattern is obtained for a material, object, device, or components thereof, at a single time point. In some embodiments, changes in infrared levels or patterns over time (e.g., by comparing at least two time points) are evaluated. In some embodiments, inherent infrared emissions of a material, object, device, or components thereof, are obtained (e.g., under defined or controlled conditions). Accordingly, in some embodiments, no external source of energy (e.g., heat or physical change) is provided (other than the temperature or other factors of the defined or controlled conditions). However, in some embodiments, infrared emissions, or dynamic time-dependent changes of infrared emissions, are obtained for materials, objects, devices, or components thereof, during or after exposure to external physical or chemical conditions. For example, infrared emissions can be measured for materials that are twisted, stretched, compressed, exposed to other shear or tension or torsion forces, or any combination thereof. In some embodiments, infrared emissions can be measured for materials that are being heated or cooled (e.g., relative to the external environment). Alternatively, infrared emissions can be measured for materials that are returning to the temperature of the environment (e.g., after exposure to a higher or lower temperature). For example, a material, object, device, or component thereof can be i) placed in a solution at a different temperature that the environmental temperature, ii) removed from the colder or hotter solution, iii) covered (e.g., sprayed) with a solution (e.g., an aqueous or other solution) that is hotter, cooler, or at the same temperature as the environment (e.g., in some embodiments, infrared emissions are measured as the solution evaporates), iv) otherwise exposed to a physical or chemical force, v) or any combination thereof. As discussed herein, in some embodiments emissivity levels, static emissivity patterns, or dynamic time-dependent emissivity patterns can be compared to reference levels or patterns to determine whether a material, object, device, or component thereof does or does not have desired physical or structural properties.

Biological and non-biological materials can be evaluated as described herein.

Biological materials can include cells, tissues, organs, or any other biological material, whether in vivo, in vitro, in a subject (e.g., a human subject), in a bioreactor, or in any other context. Non-biological materials can include liquids, solids, gases, powders, and other non-biological material. In some embodiments, the interaction between a non-biological material (e.g., a liquid, gas, powder, etc.) and a biological material can be evaluated or monitored using techniques described herein. For example, the injection of a liquid into a biological tissue can be evaluated. In some embodiments, natural or engineered biological processes (e.g., growth, development, regeneration, and/or diseases, infections or other disorders) can be detected, identified, monitored, evaluated, and/or quantified using techniques described herein. In some embodiments, physical processes that affect biological or non-biological materials (e.g., organic or non-organic materials) can be detected, identified, monitored, evaluated, and/or quantified using techniques described herein (including, for example, using emissivity differences to detect damage in materials such as metals, woods, plastic, or other biological or non-biological materials). Accordingly, differences or contrasts in emissivity can be used to detect different material and/or changes in material each of which can be indicative of desirable (e.g., growth or development) or undesirable (e.g., injury) events in a tissue or other desirable or undesirable changes in biological or non-biological materials.

It should be understood that aspects of the invention take advantage of natural emissivity and/or temperature differences that can be detected as infrared contrasts. However, it should be appreciated that techniques can be used to enhance natural infrared differences or contrasts as aspects of the invention are not limited in this respect.

In some embodiments, an infrared camera or other infrared detection device can be used to detect or measure infrared emission levels from a target material of interest (e.g., from the surface, and/or beneath the surface of synthetic scaffold, a tissue or organ, e.g., from the surface and/or beneath the surface of the skin of a subject, for example a human subject). In some embodiments, far infrared emission levels are detected. However, in some embodiments, near or mid-infrared emission levels are detected, as aspects of the invention are not limited in this respect. In some embodiments, data obtained from an infrared detection device (e.g., an infrared camera) can be analyzed on a computer to detect patterns and/or levels of infrared emissions associated with the presence and/or changes of interest (e.g., the extent of injury, disease, damage, growth, fluid injection, etc., or any combination thereof).

In some embodiments, different levels of emission are determined using a detector (e.g., an IR detector, for example a far-IR detector) that can detect and/or display small differences in the amount of IR energy emitted from an object (e.g., small differences in IR emission intensity). In some embodiments, a detector can detect difference in IR emission intensities that correlate with a temperature difference of 1° C., or less (e.g., 0.1° C., 0.01° C., or 0.001° C.). In some embodiments, a detector includes or is connected to a display that contains a palette (e.g., a color palette, a greyscale palette, an intensity palette, a heat map, or any combination thereof) that can distinguish IR emission intensities that correlate with a temperature difference of 1° C., or less (e.g., 0.1° C., 0.01° C., or 0.001° C.). In some embodiments, a detector includes a display (e.g., a high resolution display) that contains a palette (e.g., color or greyscale or a heat map or other palette) encompassing a temperature range of 0° C. to 50° C., 10° C. to 50° C., 10° C. to 40° C., 15° C. to 40° C. or 18° C. to 37° C. In some embodiments, different levels of IR emission can be detected for different materials (or different regions of that same material) even if there is no temperature difference. These different levels of emission can be indicative of different structural and/or structural properties (e.g., different surface properties) of the different materials or regions. In some embodiments, an IR detector can be calibrated to increase its sensitivity to different levels of IR emission that are not indicative of temperature differences, but rather are indicative of structural material differences (e.g., different surface structural properties).

In some embodiments, one or more infrared detectors can be associated with devices (e.g., organ or tissue bioreactors) to monitor or evaluate tissue growth or development. In some embodiments, one or more infrared detectors can be used in medical or surgical processes (e.g., for diagnostic or interventional applications as described herein).

In some embodiments, infrared levels can be displayed (e.g., on a screen of a device such as a camera, computer, or other display device) using any suitable scheme (e.g., different colors, different identifiers for different zones, or any other suitable scheme, or any combination thereof). In some embodiments, different levels of emissivity are displayed using different colors. Accordingly, color patterns can be used to evaluate differences in emissivity and identify regions of interest (e.g., tissue regions that may be characterized by desirable or undesirable activity as described herein, or areas of change or damage in objects, or other regions of interest in biological or non-biological systems). However, it should be appreciated that information output relating to detected infrared levels can be in any form that is useful for direct evaluation (e.g., visualization) by a subject, or for analysis by a computer processor, as aspects of the invention are not limited in this respect.

In some embodiments, the infrared emission information can be analyzed using a processor that is incorporated in an infrared detection device and the detected levels of infrared emission and/or the correlated information (e.g., tissue injury or damage, fluid flow, physical change, etc.) can be displayed directly on the infrared detection device (e.g., camera). For example, different levels of fluid or gas flow or tissue damage or change can be displayed (e.g., on a screen) on the detection device. In some embodiments, the infrared detection device can be a hand-held camera. However, immobilized detection devices (e.g., an immobilized camera, for example on a support such as a tripod) or larger detection devices also can be used as aspects of the invention are not limited in this respect. In some embodiments, detection devices can be head-worn (WYSIWYG). In a non-limiting example of a head worn device, one or both eyes can see IR wavelengths, visible wavelengths, and or UV wavelengths. In some embodiments, both eyes can see one or more different wavelengths (or wavelength ranges) allowing for a stereoscopic display. In some embodiments, one or more images can be displayed as overlays to provide composite views of different types of data. However, in some embodiments, infrared levels and/or associated information can be displayed on a remote display device (e.g., in direct or indirect communication with the infrared detector).

It should be appreciated that aspects of the invention are based on the natural emissivity of objects (e.g., tissue or other objects) and differences in emissivity caused by physical changes (e.g., different physical structures, surface characteristics, fluid or gas flow, movement of the material, injury, disease, damage, growth, etc.). Accordingly, no markers, dyes, or other detectable agents are required. Similarly, other detection or imaging techniques are not required. However, it also should be appreciated that aspects of the invention can be combined with other techniques that involve alternative or additional detection or imaging techniques and/or detectable markers.

In some embodiments, levels of emissivity, and, in particular, differences in levels of emissivity that are associated with different types of physical changes can be detected using an infrared detection device that is calibrated to maximize the contrast between different physical appearances rather than being calibrated to detect the temperature of an object. However, aspects of the invention are not limited in this respect, and information that is obtained using a device (e.g., camera) that is calibrated to detect temperature levels also can be analyzed to evaluate physical changes.

It should be appreciated that different forms of physical changes can be detected on the surface of an object (e.g., a tissue). For example, difference in surface texture, structure, density, hydration, reflection, and/or other properties can be detected using techniques described herein. However, it also should be appreciated that differences beneath the surface of an object can be detected provided that the surface layer is transparent (or at least partially transparent) to infrared emissions. Accordingly, structural properties and/or fluid or gas flow beneath the surface of an object or device can be detected in some embodiments, also tissue differences beneath the surface of an engineered organ or tissue can be detected, in addition to beneath the skin of a subject. These differences can be used, for example, to detect vascularization, patterns of blood flow, areas of injury, burn, bruising, wound, scarring, tissue growth or death, disease (e.g., tissue degeneration or inflammation, or other tissue damage, for example neurological degeneration, damage or scarring), or other tissue changes that can be used to detect diseases, monitor physiological activities, target injections, assist with surgery, or for other uses as aspects of the invention are not limited in this respect.

In some embodiments, aspects of the invention can be used to detect, evaluate, quantify, and/or study physiological, surgical or other interventional, and/or metabolic processes in live tissue (e.g., in organs, tissue, or cells), for example in situ in a subject, or in tissue outside a subject (for example in a bioreactor). For example, techniques described herein can be used to detect and/or analyze levels of hydration and/or vascularization in tissues or organs, physical features that may be difficult to detect using visible light (e.g., physical features with little contrast under visible light), delivery of therapeutic agents (e.g., in the form of injected fluids, sprays, other aerosols or other forms), natural or induced perfusion paths (e.g., liquid flow paths) in tissues or organs, or other biological or non-biological materials (e.g., bioreactors, injectors, microfluidic chips, etc.), or any combination thereof.

It should be appreciated that techniques described herein can be used to detect and/or analyze functional or structural differences that are impacted by (or impact) surface composition, texture, chemical make-up, thickness, tonicity, temperature, density variation, hydration variation, other physical differences that are at the surface and/or beneath the surface of a tissue, organ, or other object, and that impact the emissivity of the object.

In some embodiments, the deposition (e.g., by spray or other technique) of a substance (e.g., in the form of a powder, liquid, aerosol, or other form) on a support (e.g., a biological tissue or organ, or a non-biological support) can be monitored, evaluated, and/or quantified using techniques described herein. In some embodiments, the efficiency and/or extent of surface deposition of a material on a support can be detected using differences in emissivity between the uncovered surface and the covered surface. This can be useful, for example, in the context of coating scaffolds or other supports with one or more agents (e.g., growth factors or other agents) prior to contacting them with cells for cellularization. However, these techniques can be useful to evaluate the coating efficiency or extent of any material that results in an infrared contrast difference with the uncoated surface (this can be useful for example if no difference can be detected under visible light).

In some embodiments, the delivery (e.g., by injection other technique) of a substance (e.g., in the form liquid, suspension, or other form) to an object (e.g., a biological tissue or organ, or a non-biological object) can be monitored, evaluated, and/or quantified using techniques described herein.

In some embodiments, a tissue can be the tissue of a human subject. However, a tissue of an animal (e.g., a vertebrate, invertebrate, mammal, or other subject) can be evaluated using techniques described herein. In some embodiments, the subject is diseased or has been injured and techniques described herein are used to evaluate the extent of the injury. Accordingly, methods described herein can be used to determine whether and/or how to treat a subject based on the presence or extent of disease or injuries detected. For example, changes in blood flow can be detected and or evaluated. However, other types of disease or damage (e.g., physical or chemical damage) also can be detected and evaluated using techniques described herein.

In some embodiments, techniques described herein can be used to detect or analyze fluid flow in biological or non-biological systems. For example, changes in temperature or changes in fluid properties (different types of fluid, density, viscosity, etc.) can be detected using infrared contrast imaging. Applications include, but are not limited to detecting natural fluid flows, detecting fluid injected into an in vivo tissue site, detecting fluid injected into fluid (e.g., into blood or other biological or non-biological fluids), and/or detecting fluid injected into tissue or organ growing in a bioreactor.

In some embodiments, techniques described herein can be used to evaluate, monitor, or detect leaks in biological systems. A leak can be in vivo, for example associated with injuries or medical conditions (for example cuts, infarcts, aneurisms, etc.). An in vivo leak also can be associated with implanted material (e.g., an implanted organ or tissue, for example a blood vessel, an airway, or vascular or airflow connections associated with an implanted organ or tissue). In some embodiments, leaks can be monitored/detected in a bioreactor (e.g., associated with fluid or gas connections in a bioreactor) or within an organ or tissue growing or developing in a bioreactor (e.g., within one or more blood vessels or airways within a tissue or organ, or associated with a vascular or airway connection between the tissue or organ and conduit(s) of a bioreactor).

In some embodiments, fluid flow or other tissue differences can be detected at different depths in a material, object, device, e.g., synthetic scaffold, tissue or organ whether in vivo or in a bioreactor (for example surface differences or differences that are from 0.1 mm to several mm to several cm below the surface of the tissue or organ, for example beneath the skin or other biological surface).

However, it should be appreciated that fluid flow can be detected and analyzed in other biological or non-biological systems as aspects of the invention are not limited in this respect.

In some embodiments, changes in infrared emissivity can be enhanced or introduced into a system in order to detect or analyze a process of interest. For example, fluid flow in a biological or non-biological system can be monitored or evaluated using one or more pulses of fluid at different temperature(s), for example higher or lower temperature(s) than the temperature of the site of delivery (e.g., an injection site, a site of fluid mixing, or other site at which a fluid is being delivered). In some embodiments, one or more pulses of other material can be used (e.g., pulse(s) of material having a different physical property such as a different viscosity or other physical property that impacts the emissivity of the material) to provide a detectable contrast with the material that is being injected.

Figure 1B:
FIG. 1B illustrates the same side view as FIG. 1A, at a later time point when the zones of fluid or gas at different temperatures have progressed along the length of the conduit.

In some embodiments, temperature or other pulse(s) are adapted to be detectable by the infrared detector. In some embodiments, a series of temperature pulses of the same length (e.g., amount of fluid at a different temperature) can be used. However, in some embodiments the pulses can have different lengths. In FIG. 1, a series of pulses (e.g., temperature pulses) are illustrated in a side view of a conduit (10) as viewed by infrared imaging (e.g., wherein the infrared signal of the different fluid or gas temperatures or viscosities are detectable via infrared through the wall of the conduit. The direction of fluid or gas flow into the conduit is indicated by arrow (12). The temperature (and/or viscosity or other property detectable by infrared contrast analysis) of the fluid or gas that is flowing into the conduit is alternated between two different temperatures illustrated as zones of fluid or gas at a first temperature (14) and a second different temperature (16). In FIG. 1A, the fluid or gas at the second temperature (16) is introduced as a series of four pulses. It should be appreciated that the amount of fluid or gas that is introduced in each pulse can be different as aspects of the invention are not limited in this respect. Accordingly, the width of each zone of fluid or gas at a second temperature (e.g., relative to each other and/or relative to the fluid or gas at the first temperature) can vary. It also should be appreciated that a single pulse at a second temperature can be used, or more than four pulses (e.g., 5-10, 10-50, or a continuous series of pulses) can be used as aspects of the invention are not limited in this respect. It also should be appreciated that the second temperature can be higher or lower than the first temperature. Also, pulses of fluid or gas at a series of different temperatures can be used (not all the pulses are necessarily at the same second temperature although they can be in some embodiments). In some embodiments, the temperature differences between different zones of fluid or gas are used to detect the different zones using an infrared detector. In FIG. 1B, the pulses of the second temperature have moved in the direction of flow (towards the right of the figure). In some embodiments, it can be determined that fluid or gas is flowing in the conduit by observing the movement of one or more pulses of fluid or gas at a second temperature. In some embodiments, the rate of flow can be determined by determining the rate of movement of the fluid or gas that is at the second temperature. It should be appreciated that similar analyses can be performed for other properties (e.g., different viscosities) that can be detected by infrared contrast analysis as described herein. It also should be appreciated that this analysis can be used to evaluate flow in a conduit in a scaffold, or flow in a tube or other conduit in a bioreactor, or flow through a fluid connection between a scaffold and a bioreactor or a combination thereof, as aspects of the invention are not limited in this respect.

Figure 2A:
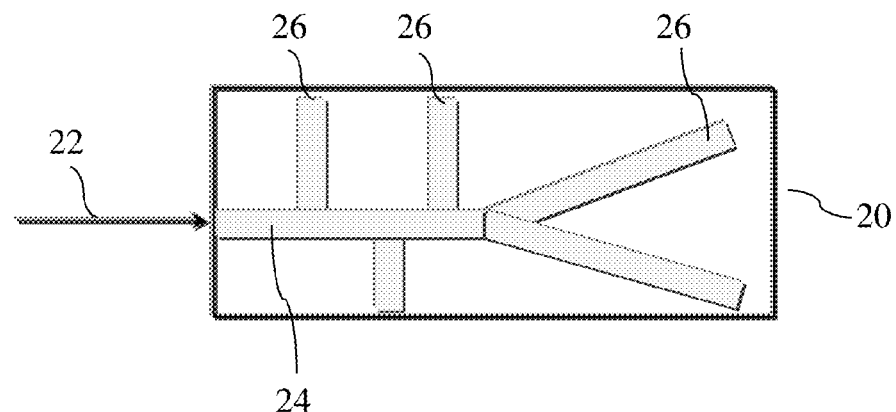
FIG. 2A illustrates a non-limiting embodiment of a side view of a synthetic scaffold containing a network of conduits for fluid or gas flow, the temperature within the network of conduits is uniform as seen by infrared imaging.
Figure 2B:
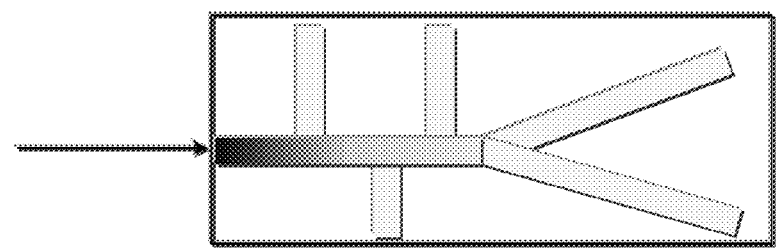
FIG. 2B illustrates the same view as FIG. 2A upon initial introduction of a fluid or gas at a different temperature (e.g., higher or lower than the conduit temperature) as seen by infrared imaging showing an initial change in temperature near the site of introduction.
Figure 2C:
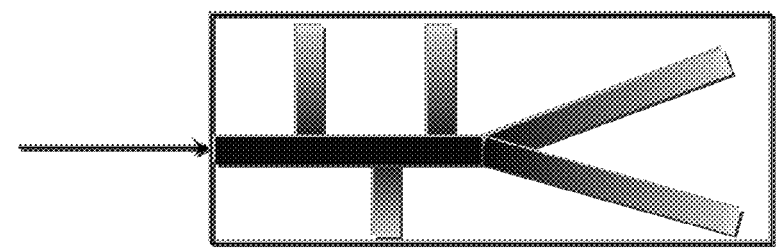
FIG. 2C illustrates the same view as FIG. 2B after the fluid or gas at a different temperature has filled the main channel of the conduit network and is filling the branches of the conduit network, as seen by infrared imaging.

In some embodiments, pulses of temperature can be used to evaluate the extent or efficiency of perfusion of an object (e.g., a synthetic scaffold). FIG. 2 illustrates a non-limiting embodiment of a side view of an object or device (20), for example a synthetic scaffold, that contains a conduit network. The direction of fluid or gas flow into the conduit (e.g., via a connection to a conduit in a bioreactor such as a tube that is connected to a pump that pumps fluid or gas, for example from a reservoir) is shown by arrow (22) in FIG. 2A. In some embodiments, the object or device (20) can be a synthetic scaffold that incorporates the network of conduits (e.g., conduits that are used to perfuse the scaffold during tissue or organ growth). In some embodiments, the network of conduits is visible via infrared imaging through the wall of the object or device. In some embodiments, the network is visible due to difference in the structure of the material forming the conduit. In some embodiments, the flow of fluid or gas through the conduit network results in different infrared emission levels (e.g., even if the temperature of the fluid or gas is the same as the conduit and device/object) that make the conduit network visible by infrared imaging. In some embodiments, the flow of fluid or gas (e.g., into an empty conduit network) or the flow of fluid or gas having a different temperature, viscosity, or other property visible by infrared contrast imaging, than that of existing fluid or gas in the conduit can be evaluated as illustrated in FIGS. 2A, 2B and 2C. In the object or device of FIG. 2A, fluid or gas flows into the network of conduits in a direction shown by arrow (22). Fluid flows into a primary conduit (24) and through primary conduit (24) into branch conduits (26) that are in fluid connection with primary conduit (24). In FIG. 2B, the initial influx of new gas or fluid (e.g., that is detectable due to a different temperature, viscosity, or other property) is illustrated by the darker shading that appears from the input at the end of the arrow in primary conduit (24). This new gas or fluid that is input to the network subsequently spreads to the branches of the conduit network (26) as illustrated in FIG. 2C. If there is a leak or if the input gas or fluid does not spread evenly throughout the network (e.g., it misses one or more branches of the network, or portions thereof), then this can be detected by an aberrant infrared image. It should be appreciated that in some embodiments a conduit network include permeable regions (e.g., at the ends of the branches). In this case, input fluid or gas should be detectable outside of the conduits at regions of permeability. Accordingly, aspects of the invention also can be used to confirm the appropriate permeability properties of a synthetic scaffold and/or the appropriate perfusion of an engineered tissue or organ during growth and development.

It should be appreciated that by following and or quantifying the pulses, flow patterns, or other changes in infrared images, the efficiency and/or amount of material being delivered through a conduit in a bioreactor and/or synthetic scaffold, and the amount or efficiency of delivery to one or more regions of an engineered tissue or organ can be assessed. In some embodiments, a fluid is being delivered to a biological site (e.g., a site of injection of a therapeutic fluid in a body or to a tissue or organ in a bioreactor). In some embodiments, a first fluid is being delivered to a second fluid, and the flow can be monitored or evaluated using techniques described herein. In some embodiments, the amount of fluid at a different temperature is selected so that is does not significantly alter the temperature of the fluid being delivered (and/or the site of delivery or the second fluid that a first fluid is delivered to). This can reduce the loss of infrared contrast due to fluid mixing or temperature changes.

Accordingly, in some embodiments of a fluid delivery (e.g., a perfusion), in order to maintain resolution and high contrast in an image, temperature pulse(s) can be sent in a time and volume segmented fashion. The ratio of hot and/or cold and the time duration can be related to the thermal coiffing of the objects being viewed, for example, such that the hot and cold cycles prevent the substrate from getting hot or cold during the duration and volume delivered at a certain temperature. For example, the flow of infusion or perfusion can be segmented with a flow of a temperature that depending on the thermal coefficient of absorption and radiation will not destroy the contrast by emissions cause by angular differences caused by surface finish, material density etc. of the delivery site being monitored. Accordingly, in some embodiments, the temperature effect does not overpower the contrast of the objects that are submerged, flowed over or through. In some embodiments, solution(s) of different temperature are used to cause contrast without deteriorating the temperature effect of detected emissions.

In some embodiments, an infrared detector is calibrated to detect one or more threshold levels of temperature difference that correspond to the temperature difference(s) between the fluid being injected and the site of injection.

It should be appreciated that when colors are used to display infrared signals detecting using techniques described herein, the color palette selections can make a large difference in what is seen. In some embodiments, different colors can be selected to identify different types of contrast that can be detected and that can be indicative of different processes that are occurring in an object of interest. For example, different colors could be selected to identify blood leaks as opposed to scarring or other physiological or physical changes (e.g., to highlight blood flow, a palette could be selected to not show color changes between 18 and 10° C. or between 25 and 50° C., or between 37 and 50° C. In some embodiments, resolution the range being displayed can have different levels of sensitivity (for example, less than 0.5° C.). However, it should be appreciated that different ranges of resolution (and different color palettes for different levels of sensitivity) can be used depending on the levels and patterns of infrared emissions that are being evaluated.

In some embodiments, emissions (e.g., IR emissions) from a synthetic scaffold, engineered tissue, or other material can be used to evaluate one or more structural and/or functional properties of the material. In some embodiments, relative emission intensities (e.g., relative IR emission intensities) from different areas of a synthetic scaffold, engineered tissue, or other material can be used to evaluate one or more structural and/or functional properties of the material. In some embodiments, the rate of change of emission intensity as a function of physical position within a synthetic scaffold, engineered tissue, or other material can be used to evaluate one or more structural and/or functional properties of the material. It should be appreciated that emission intensities (e.g., relative emission intensities) can be analyzed using any suitable method. In some embodiments, emission levels are analyzed and/or displayed (e.g., using a color display), in some embodiments, changes in emission levels are analyzed and/or displayed. In some embodiments, methods described herein can be used to identify areas of structural or functional change, areas of structural or functional weakness, or areas having other properties of interest. In some embodiments, a change in the level of emission (e.g., a change in IR emission level) over time at a position of interest on a material can be used to identify a structural or functional change at that position. In some embodiments, a change in the level of emission (e.g., a change in IR emission level) as a function of position on a material can be used to identify different regions of the material, wherein the different regions have different structural or functional properties. In some embodiments, a transition from a first region to a second region can be identified as the zone where the level of emission changes. It should be appreciated that a change in emission can be an increase or a decrease in emission levels. In some embodiments, a pattern of different levels of emission can be used to characterize a material of interest. In some embodiments, a pattern that is characteristic of desired functional or structural properties of a material can be used as a reference pattern to which patterns obtained for other materials can be compared. For example, a reference pattern of IR emission levels obtained for a synthetic scaffold of interest (e.g., a scaffold known to have acceptable functional or structural properties) can be used to evaluate other synthetic scaffolds (e.g., subsequent synthesized scaffolds) to determine whether they have the same or similar patterns indicating that they also have acceptable functional or structural properties. Accordingly, aspects of the invention can be useful in the production of materials (e.g., synthetic scaffolds) to determine whether they have desired properties. In some embodiments, materials (e.g., synthetic scaffolds) that do not have appropriate emission patterns are not used (e.g., for tissue engineering). It should be appreciated that patterns of emission can be evaluated visually (e.g., by looking at a display such as a screen or a printed document that shows different levels of emission). However, in some embodiments patterns of emission can be represented and/or evaluated quantitatively (e.g., using data analysis software and/or using mathematical representations of the emission levels). For example, an area under the curve representing the emission level for one or more regions of interest can be calculated. In some embodiments, the slope of infrared emission change between a first region and a second region of a material is determined. In some embodiments, a profile of relative infrared emission levels is determined across a line segment (e.g., a stretch of connected pixels) spanning a portion of 2D or 3D image of a material or surface thereof. In some embodiments, the line segment spans multiple regions of a material of interest. However, it should be appreciated that any technique may be used to quantify different regions of emission intensity. This allows any changes or differences to be evaluated quantitatively (e.g., to determine quantitative differences between different levels and/or patterns of IR emission).

In some embodiments, patterns of IR emissivity for a material can be evaluated at a selected time of interest. In some embodiments, the patterns of emissivity can be evaluated over time (e.g., by detecting an IR pattern at two or more time points and comparing the patterns to detect any changes as a function of time). In some embodiments, changes can be evaluated over a few hours or over several days or weeks (e.g., 1-6, 6-12, 12-18, 18-24 hours, 2-7 days, 1-4 weeks, or over 2 or more months).

In some embodiments, an IR pattern can be assessed by, for example, analyzing the slope of change in levels of emissivity along one or more directions over at least one surface region of a material of interest (e.g., in one or more directions radiating out from a region of low or high IR emission). In some embodiments, vectors representing the rate of change of IR emissivity can be determined. In some embodiments, an infrared detection device is calibrated to detect different temperatures. However, in some embodiments, an infrared detection device is calibrated to be sensitive to different levels of IR emissivity that can be affected by surface properties independent of temperature. Accordingly, an infrared detection device can be calibrated to detect contrasts between different surface properties (e.g., whether they are shiny or not, or other surface properties) that can be detected even if they have the same temperature. Accordingly, an infrared camera (e.g., a forward looking IR camera or detector) or other infrared detection device can be calibrated to be sensitive to surface contrasts between different tissue regions (e.g., calibrated or limited to detect particular IR ranges, for example far IR or subsets of wavelength ranges within the far IR). In some embodiments, a detector device include two or more detectors, for example each for a different type of IR (e.g., two or three of near, mid, or far IR). In some embodiments, a detector device includes a single detector that can detect two or more types of IR (e.g., two or three of near, mid, or far IR).

It should be appreciated that different IR spectra can be evaluated. In some embodiments, near IR is evaluated. In some embodiments, mid-IR is evaluated. In some embodiments, far IR is evaluated. In some embodiments, two or more are evaluated. In some embodiments, IR patterns are evaluated and or overlaid with other information (e.g., visible or UV patterns or images). In some embodiments, mid-IR data can be detected by using a suitable detector and a suitable excitation energy. If two or more detectors are used, they can be aligned to allow the images or data to be overlaid.

In some embodiments, the amount of IR radiation that is emitted from a material (e.g., a synthetic scaffold) is measured using a device (e.g., a camera) that provides (e.g., displays) apparent temperatures of the material. However, other devices and techniques for detecting, measuring, or displaying the amount of IR radiation also can be used as aspects of the invention are not limited in this respect. In some embodiments, absolute levels of radiation do not need to be calculated, determined, and/or displayed, because differences in material property can be determined based only on relative amounts of IR radiation for different portions of the material (e.g., of the synthetic scaffold).

In some embodiments, an infrared camera or other infrared detection device can be used to detect or measure infrared emission levels from a target material of interest (e.g., from the surface of a synthetic scaffold for tissue engineering). In some embodiments, far infrared emission levels are detected. However, in some embodiments, near or mid-infrared emission levels are detected, as aspects of the invention are not limited in this respect. In some embodiments, data obtained from an infrared detection device (e.g., an infrared camera) can be analyzed on a computer to detect patterns and/or levels of infrared emissions associated with structural or functional properties of interest or with unwanted structural or functional properties (e.g., due to incorrect synthesis or damage of the material). These levels can be displayed (e.g., on a screen of the computer) using any suitable scheme (e.g., different colors, different identifiers for different zones, or any other suitable scheme, or any combination thereof). In some embodiments, the infrared emission information can be analyzed using a processor that is incorporated in the infrared detection device and the detected levels of infrared emission and/or the correlated levels of material property can be displayed directly on the infrared detection device (e.g., camera).

In some embodiments, the infrared detection device can be a hand-held camera (e.g., a forward looking infrared camera). However, immobilized detection devices (e.g., an immobilized camera, for example on a support such as a tripod) or larger detection devices also can be used as aspects of the invention are not limited in this respect. In some embodiments, a device is attached to or incorporated into one or more components of a bioreactor (e.g., within a chamber and/or within one or more conduits of a bioreactor, for example integrated into the wall of a chamber or a conduit or otherwise affixed within a chamber or conduit). In some embodiments, a device can detect only one type of IR radiation (e.g., near, mid, or far). However, in some embodiments, a device can detect two or more types of IR radiation. In some embodiments, two or more different devices can be used. Information corresponding to different types of IR radiation can be overlaid and or combined with other information including for example visual or UV information.

In some embodiments, aspects of the invention relate to using infrared patterns to evaluate synthetic scaffold and/or bioreactor properties based on surface infrared emission levels and/or distributions without requiring any dyes, labels, or energy input. In some embodiments, no irradiation is required since techniques described herein do not rely on reflected IR. For example, far IR data corresponding to thermal radiation can be obtained without using a dye or excitation energy. However, in some embodiments, one or more dyes or excitation energies can be used. For example, mid IR data can be obtained using an appropriate excitation energy in addition to a mid IR detector.

In some embodiments, the infrared radiation emission that is detected and/or analyzed is a far infrared radiation emission. In some embodiments, the far infrared wavelengths that are detected and/or analyzed are 15-1,000 µm. However, other infrared wavelengths also may be detected and/or analyzed.

In some embodiments, the infrared emissions utilized (e.g., collected and/or evaluated) with the methods and devices disclosed herein have a wavelength in the range of 0.7 µm to 25 µm or 8 µm to 25 µm. In some embodiments, the infrared emissions comprise emissions in the near infrared range, e.g., emissions having a wavelength of about 0.7 µm to about 1.0 µm. In some embodiments, the infrared emissions comprise emissions in the short-wave infrared range, e.g., emissions having a wavelength of about 1 µm to about 3 µm. In some embodiments, the infrared emissions comprise emissions in the mid-wave infrared range, e.g., emissions having a wavelength of about 3 µm to about 5 µm. In some embodiments, the infrared emissions comprise emissions in the long-wave infrared range, e.g., emissions having a wavelength of about 8 µm to about 12 µm, or about 7 µm to about 14 µm. In some embodiments, the infrared emissions comprise emissions in the very-long wave infrared range, e.g., emissions having a wavelength of about 12 µm to about 30 µm. In some embodiments, the infrared emissions comprise emissions in the far infrared, e.g., emissions having a wavelength of about 15 µm to about 1000 µm.

It should be appreciated that aspects of the invention are based on the natural emissivity of biological and non-biological material and differences in emissivity caused by structural or functional differences. Accordingly, no markers, dyes, or other detectable agents are required in some embodiments. Similarly, Doppler or other acoustic techniques also are not required in some embodiments. However, it also should be appreciated that aspects of the invention can be combined with other techniques that involve Doppler and/or other acoustic techniques and/or detectable markers.

In some embodiments, the levels of emissivity, and, in particular, differences in the levels of emissivity that are associated with different types or degrees of structural or functional properties can be detected using an infrared detection device that is calibrated to maximize the contrast between different material appearances (e.g., surface appearances) rather than being calibrated to detect the temperature of a material. Accordingly, IR contrast imaging can be performed by calibrating an IR detector to be most sensitive to contrasts between different IR levels that are associated with a structural or functional property of interest. In some embodiments, a high resolution palette can be used to display different levels of IR emission that may not be distinguishable using typical display palettes that do not provide sufficient contrast (e.g., between IR levels corresponding to physiological injuries or conditions, for example, corresponding to 0-50° C., around 25-50° C.). However, aspects of the invention are not limited in this respect, and information that is obtained using a device (e.g., camera) that is calibrated to detect temperature levels also can be analyzed to evaluate the level or pattern of structural or functional properties of interest.

In some embodiments, infrared levels or patterns can be used to evaluate structural or functional properties of a synthetic scaffold and/or one or more components of a bioreactor (e.g., a chamber wall, a conduit, or any other component or combination thereof), including, for example, a polymeric material, a fibrous material, a metal material, a plastic material, a rubber material, any other material, or any combination thereof.

In some embodiments, patterns of functional and/or structural properties can be determined based on the contrast (e.g., infrared contrast, for example, near, mid, or far infrared contrast) between different parts of a material being analyzed. In some embodiments, it is not the absolute level of emission that is used to determine structural or functional properties, rather differences in emission between different regions can be used to identify or determine the presence of functional or structural differences that may be indicative of potential defects in a synthetic scaffold and/or bioreactor or other material. However, in some embodiments, reference levels or patterns of emission can be established for normal synthetic scaffolds and/or bioreactors or other materials, and other reference levels or patterns of emission can be established for defective material.

In some embodiments, different emissions (e.g., different levels or patterns of infrared emissions) from different regions of a material can reflect differences in surface structure and/or function. However, it also should be appreciated that structural and/or functional differences beneath a material surface also can change the emission patterns (e.g., infrared emission patterns) of a material. Accordingly, patterns of emission changes (e.g., contrasts in emission levels) can be used to evaluate surface and/or deeper material properties.

Aspects of methods for evaluating IR image data disclosed herein may be implemented in any of numerous ways. For example, the various methods or processes outlined herein may be coded as software that is executable on one or more processors that employ any one of a variety of operating systems or platforms. Such software may be written using any of a number of suitable programming languages and/or programming or scripting tools, and also may be compiled as executable machine language code or intermediate code that is executed on a framework or virtual machine. The MATLAB image processing toolbox (The MathWorks, Inc., Natick, Mass.) is an exemplary, but non-limiting, system that may be used for implementing certain aspects of the methods disclosed herein.

In this respect, aspects of the invention may be embodied as a computer readable medium (or multiple computer readable media, e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed herein. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs, which when executed perform certain methods disclosed herein, need not reside on a single computer or processor, but may be distributed in a modular fashion among or between a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

In some embodiments, aspects of the invention relate to evaluating fluid flow in a bioreactor. In some embodiments, a bioreactor comprises a chamber. The chamber may include a first inlet port and a first outlet port in fluid communication with the chamber. In some embodiments, the chamber may have two or more inlet ports, two or more outlet ports, or any combination thereof as described in more detail herein. It should be appreciated that in some embodiments, one or more ports may act both as inlet and outlet ports by being configured to allow fluid flow into the chamber or out of the chamber. The control of fluid flow into or out of the chamber may be determined by a pump, a valve, a difference in pressure, or any other mechanism or factor that controls the direction of fluid flow (e.g., through one or more conduits connected to the inlet or outlet ports). In some embodiments, aspects of the invention relate to using infrared emission levels to determine whether a synthetic scaffold is appropriately attached to a bioreactor (e.g., that there are no leaks or that the leaks are not excessive at one or more sites of attachment of a scaffold conduit—for example an airway or vascular connection to a bioreactor inlet or outlet.

Aspects of the invention can be used to evaluate synthetic scaffolds that are prepared for tissue engineering (e.g., that are cellularized and positioned within a chamber of a bioreactor to generate artificial tissue). In growing tissues and/or organs of the body, different types of cells can be arranged proximate a scaffold in sophisticated organizations or architectures that are responsible for the complex functions of the tissue or organ. Thus, architectures having dimensions and arrangements closely related to the natural conditions of the tissue or organ can be formed. The design of the scaffold and the arrangement of cells within the scaffold can allow functional interplay between relevant cells, e.g., between cells cultured on the scaffold and those of the host environment. These factors may also enable appropriate host responses, e.g., lack of blood clotting, resistance to bacterial colonization, and normal healing, when implanted into a mammalian system. In some embodiments, aspects of the invention are used to observe and/or evaluate patterns of cellularization of a synthetic scaffold.

A variety of different scaffolds can be used for seeding, growing, supporting, or maintaining cells, tissues, and organs as described herein. A scaffold can have any suitable shape and may depend on the particular tissue and/or organ to be grown. For example, the scaffold may be substantially tubular, substantially cylindrical, substantially spherical, substantially planar, substantially ellipsoidal, disk-like, sheet-like, or irregularly shaped. The scaffold can also have branching structures, e.g., to mimic arteries, veins, or other vessels. In certain embodiments, at least a portion of the scaffold is hollow. In some embodiments, a scaffold may include one or more conduits (e.g., channels, pathways, tubes, etc.) for gas or liquid transport. In some embodiments, a conduit in a scaffold is for an airway or vascular structure in a tissue or organ being engineered. However, in some embodiments, a conduit is during tissue engineering to provide a pathway for fluids, cells, nutrients, growth factors, waste, or other materials that need to be perfused into or removed from a tissue or organ scaffold to promote and support appropriate cell growth and development. In some embodiments, these types of conduits are useful for tissue or organ growth, but are no longer used after implantation into a host. It should be appreciated that the size and properties of a conduit will depend on its intended use. In some embodiments, a conduit may include certain portions that are more permeable than others. For example, a branched conduit (e.g., as illustrated in FIG. 2) that is used for perfusing a synthetic scaffold during tissue engineering may include one or more permeable regions in order to promote the delivery of desired molecules or cells to target regions of interest in a scaffold. In some embodiments, the ends of the branched conduit are more permeable than the trunks and branches of the conduit structure. However, other configurations and patterns of relative permeability for different types of molecules can be used as aspects of the invention are not limited in this respect. In some embodiments, regardless of the type of conduit, the properties of the conduits can be evaluated using techniques described herein to make sure that they are appropriate for cellularization and/or subsequent implantation.

In some embodiments, scaffolds may be formed of natural and/or artificial materials. Materials used to form scaffolds may be biocompatible, and can include synthetic or natural polymers, inorganic materials (e.g., ceramics, glass, hydroxyapatite and calcium carbonate), composites of inorganic materials with polymers, and gels. All or a portion of a scaffold may be formed in a material that is non-biodegradable or biodegradable (e.g., via hydrolysis or enzymatic cleavage). In some embodiments, biodegradable polyesters such as polylactide, polyglycolide, and other alpha-hydroxy acids can be used to form scaffold. By varying the monomer ratios, for example, in lactide/glycolide copolymers, physical properties and degradation times of the scaffold can be varied. For instance, poly-L-lactic acid (PLLA) and poly-glycolic acid (PGA) exhibit a high degree of crystallinity and degrade relatively slowly, while copolymers of PLLA and PGA, PLGAs, are amorphous and rapidly degraded. A portion of a scaffold that is biodegradable may, in some embodiments, degrade during the growth of cells, tissues and/or organs in the bioreactor. In other embodiments, degradation may take place after implanting the tissue or organ in a recipient.

Methods described herein can be used for evaluating scaffolds that include one or more components that are made using any suitable technique (e.g., by electrospinning, electrospraying, molding, casting, printing, lithography, or any combination thereof).

In some embodiments, scaffolds comprise one or more types of fiber (e.g., nanofibers). In some embodiments, scaffolds comprise one or more natural fibers, one or more synthetic fibers, one or more polymers, or any combination thereof. It should be appreciated that different material (e.g., different fibers) can be used in methods and compositions described herein. In some embodiments, the material is biocompatible so that it can support cell growth. In some embodiments, the material is permanent (e.g., PET), semi-permanent (e.g., it persists for several years after implantation into the host, or rapidly degradable (e.g., it is resorbed within several months after implantation into the host).

In some embodiments, the scaffold contains or consists of electrospun material (e.g. macro or nanofibers). In some embodiments, the electrospun material contains or consists of PET (polyethylene terephthalate (sometimes written poly (ethylene terephthalate)). PET is a thermoplastic polymer resin of the polyester family. PET consists of polymerized units of the monomer ethylene terephthalate, with repeating C10H8O4 units. Depending on its processing and thermal history, polyethylene terephthalate may exist both as an amorphous (transparent) and as a semi-crystalline polymer. The semicrystalline material might appear transparent (particle size <500 nm) or opaque and white (particle size up to a few microns) depending on its crystal structure and particle size. Its monomer (bis-β-hydroxyterephthalate) can be synthesized by the esterification reaction between terephthalic acid and ethylene glycol with water as a byproduct, or by transesterification reaction between ethylene glycol and dimethyl terephthalate with methanol as a byproduct. Polymerization is through a polycondensation reaction of the monomers (done immediately after esterification/ transesterification) with water as the byproduct. In some embodiments, the electrospun material contains or consists of polyurethane (PU). In some embodiments, the electrospun material contains or consists of PET and PU.

In some embodiments, the artificial scaffold may consist of or include one or more of any of the following materials: elastic polymers (e.g., one or more polyurethanes (PU), for example polycarbonates and/or polyesters), acrylamide polymers, Nylon, resorbable materials (e.g., PLGA, PLA, PGA, PCL), synthetic or natural materials (e.g., silk, elastin, collagen, carbon, gelatin, chitosan, hyaluronic acid, etc.) or any combination thereof. In some embodiments, the scaffold may consist of or include addition polymer and/or condensation polymer materials such as polyolefin, polyacetal, polyamide, polyester, cellulose ether and ester, polyalkylene sulfide, polyarylene oxide, polysulfone, modified polysulfone polymers and mixtures thereof. In some embodiments, the scaffold may consist of or include polyethylene, polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinylalcohol in various degrees of hydrolysis (e.g., 87% to 99.5%) in cross-linked and non-cross-linked forms. In some embodiments, the scaffold may consist of or include block copolymers. In some embodiments, addition polymers like polyvinylidene fluoride, syndiotactic polystyrene, copolymer of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly (methyl methacrylate) and its various copolymers, and PET (polyethylene terephthalate (sometimes written poly(ethylene terephthalate))) can be solution spun or electrospun and combined with any other material disclosed herein to produce a scaffold. In some embodiments, highly crystalline polymers like polyethylene and polypropylene may be solution spun or combined with any other material disclosed herein to produce a scaffold.

A scaffold may, in some cases, be formed of a biological material, such as a tissue construct. In certain embodiments, at least a portion of the tissue construct is acellular. In certain embodiments, the at least partially acellular tissue construct comprises tissue that has been decellularized. In some cases, combinations of natural and artificial materials can be used.

Appropriate systems and techniques for fabricating scaffolds include, but are not limited to, molding, three-dimensional printing (e.g., three-dimensional layering), electrospinning, multi-photon lithography, stereolithography (SLA), selective laser sintering (SLS) or laser ablation, ballistic particle manufacturing (BPM), fusion deposition modeling (FDM), or any combination of two or more thereof. However, other fabrication techniques also can be used.

Scaffolds may be porous or substantially nonporous. In some instances, the wall of a scaffold includes pores having a cross-sectional dimension of less than or equal to 1 mm, less than or equal to 100 microns, less than or equal to 50 microns, less than or equal to 40 microns, less than or equal to 30 microns, less than or equal to 10 microns, less than or equal to 5 microns, less than or equal to 1 micron, or less than or equal to 100 nm. A variety of techniques can be used for introducing porosity into a scaffold. For instance, porosity can be induced by methods such as solution casting, emulsion casting, polymer blending, and phase transition induced porosity. In some embodiments, a scaffold can be coated with a porous material (e.g., a polymer such as a gel), e.g., prior to or during the seeding of cells. A porous polymer coating a scaffold can be used for a variety of purposes. For example, a porous polymer may be used to form pores on a scaffold that is otherwise non-porous. The porous polymer may allow, for example, sustained release of an active agent from the scaffold, e.g., to facilitate cell growth and/or cell adhesion as a function of time. In some embodiments, aspects of the invention can be used to evaluate the porosity of a scaffold. In some embodiments, the size and distribution of pores in a synthetic tissue scaffold can be detected using an IR detector, even if the scaffold is maintained at a uniform temperature, because the contrasting structural properties (e.g., surface properties) of the pores and the surrounding material can be detected as different IR emissivity levels. However, in some embodiments the temperature of a scaffold can be increased or decreased and the resulting IR changes can be detected and evaluated. In some embodiments, a pore changes temperature (e.g., heats or cools) at a different rate (e.g., faster or slower) than surrounding material. This difference can be used to identify and evaluate the pore size and distribution in a synthetic material.

In some embodiments, one or more scaffold components can be thin sheets, cylinders, thick ribs, solid blocks, branched networks, etc., or any combination thereof having different dimensions. In some embodiments, the dimensions of a complete and/or assembled scaffold are similar or identical to the dimension of a tissue or organ being replaced. In some embodiments, individual components or layers of a scaffold have smaller dimensions. For example, the thickness of a nanofiber layer can be from several nm to 100 nm, to 1-1000 microns, or even several mm. However, in some embodiments, the dimensions of one or more scaffold components can be from about 1 mm to 50 cms, or larger, smaller, or of intermediate size.

Accordingly, it should be appreciated that scaffolds can have various dimensions which may depend on the particular use of the scaffold. A scaffold may have an average thickness of, for example, between 1 micron and 1 mm, between 10 microns and 0.5 mm, between 1 mm and 5 cm, between 1 mm and 1 cm, between 1 cm and 10 cm, or between 1 cm and 5 cm. Other thicknesses are also possible. The largest cross-sectional dimension of the scaffold can also vary from, for example, between 1 micron and 1 mm, between 10 microns and 0.5 mm, between 1 mm and 5 cm, between 1 mm and 1 cm, between 1 cm and 10 cm, between 1 cm and 5 cm, between 1 cm and 20 cm, or between 10 cm and 20 cm. A length of the scaffold can also vary from, for example, between 1 mm and 5 cm, between 1 cm and 10 cm, between 1 cm and 5 cm, between 1 cm and 20 cm, or between 10 cm and 20 cm. Other lengths are also possible. A scaffold may also have an aspect ratio (length to average cross sectional dimension) of at least 2:1, 3:1, 5:1, or 10:1 or more. It also should be appreciated that the size and thickness of a scaffold may vary over its shape (e.g., length, width, etc.). In some embodiments, a scaffold may include a series of zones of different thicknesses (e.g., forming a pattern of different thicknesses that may provide different structural properties). In some embodiments, thicknesses differences (and/or other structural features of a scaffold) can be detected as differences in IR emissivity in different regions of the scaffold.

It also should be appreciated that scaffolds may include one or more conduits or other structures that can be incorporated, for example, into the wall of a scaffold.

In some embodiments, surface properties of a scaffold can be modified by various techniques. For example, in some cases, surfaces of a scaffold can be modified by coating and/or printing an additive proximate the structure. Surfaces may be modified with additives such as proteins and/or other suitable surface-modifying substances. For example, collagen, fibronectin, an RGD peptide, and/or other extracellular matrix (ECM) proteins or growth factors can be coated onto the scaffold, e.g., to elicit an appropriate biological response from cells, including cell attachment, migration, proliferation, differentiation, and gene expression. In some embodiments, the extent and/or degree of surface modification can be detected and/or evaluated based on differences in IR emission levels of modified relative to un-modified surfaces. It should be appreciated that the IR emission of a modified surface can be higher or lower than an unmodified surface, depending on the nature of the scaffold material and the type of surface modification that is being evaluated. Aspects of the invention can be used to screen and evaluate synthetic scaffolds that are produced for tissue engineering purposes. Accordingly, aspects of the invention can be used for quality control processing of large or industrial scale production of synthetic scaffolds or scaffold material.

In some embodiments, cells can be seeded onto surfaces of a scaffold. In one embodiment, cell adhesion proteins can be incorporated into certain portions of a scaffold to facilitate ingrowth of blood vessels. In another embodiment, growth factors can be incorporated into the scaffold to induce optimal cell growth conditions that trigger healthy tissue formation within certain regions of the scaffold. In other cases, additives can be incorporated into the material used to form the scaffold (e.g., embedded in the scaffold during fabrication). In some cases, it may be desirable to modify all or portions of a scaffold with a material that inhibits cell adhesion, such as a surfactant (e.g., polyethylene glycol and polypropylene oxide-polyethylene oxide block copolymers). For instance, areas of a scaffold where it is not desirable for cellular growth can be coated with such materials, e.g., to prevent excessive soft connective tissue ingrowth into the structure from the surrounding tissue. In some cases, modification of surface properties of the scaffold can be used to position cells at specific sites on or within the scaffold. In some embodiments, a combination of cell-adhering and cell-inhibiting substances can be incorporated into various portions of a scaffold to simultaneously facilitate and inhibit cell growth, respectively. Aspects of the invention can be used to evaluate cellularization of a scaffold based on the IR signal or pattern that is emitted from the surface of the scaffold being evaluated (e.g., a scaffold undergoing cellularization).

As described herein, cells may be seeded on various portions of a scaffold either before or after the scaffold is positioned in a bioreactor. In certain embodiments, cells may be seeded on at least one surface or region of a scaffold (e.g., a decellularized tissue construct) such that the cells are contained within at least one structural region of a bioreactor defined by a scaffold. In certain embodiments, cells are seeded on two or more regions or surfaces of a scaffold. In certain such embodiments, the cells on the first region or surface are of the same type as the cells on the second region or surface and in other embodiments they are of different types. In certain embodiments, at least one of the cell types on at least one of the first and second region or surface is of a type normally associated with the type of tissue comprising a decellularized tissue construct in vivo. It should be appreciated that the cell types used to seed a bioreactor should be selected based on the type of tissue or organ structure that is being grown. In some embodiments, the cells may be epithelial, endothelial, mesothelial, connective tissue cells, fibroblasts, etc., or any combination thereof. In some embodiments, cells may be stem cells, or pluripotent or totipotent cells. In some embodiments, different cells may be used to seed different portions of a scaffold. In some embodiments, one or more growth factors may be provided to promote appropriate growth and/or differentiation of the cells. In some embodiments, the extent and/or pattern of cellularization can be evaluated by obtaining and/or analyzing an IR signal or pattern. In some embodiments, the IR signal or pattern can be compared to one or more reference signals or patterns that are characteristic of known extents or types of cellularization. Based on the comparison, the extent or pattern of cellularization can be determined. In some embodiments, if the cellularization level or pattern is sufficient, the cellularized scaffold is used (e.g., implanted into a host). In some embodiments, if the cellularization level is insufficient, the scaffold is further cellularized or incubated in a bioreactor. Alternatively, in some embodiments, a scaffold that is not appropriately cellularized is discarded and not used for implantation into a patient.

As described herein, aspects of the invention can be used to evaluate scaffolds prior to seeding or attachment to a bioreactor. However, aspects of the invention also can be used to evaluate scaffold attachment to a bioreactor (e.g., to detect leaks or to detect insufficient fluid flow through a scaffold in a bioreactor). In addition, structural properties of bioreactor components, and/or patterns of fluid flow through one or more bioreactor components (e.g., pumps, tubes, valves, reservoirs, etc., or any combination thereof) can be monitored or evaluated to detect leaks or patterns of incorrect or insufficient fluid or gas flow. Bioreactor devices or components described herein may be configured for monitoring and/or modulating the growth conditions of an engineered tissue or organ. A device for growing an engineered tissue or organ can include a chamber. The chamber can have any suitable size and/or shape. A chamber may include one or more sealable openings that can be used to introduce a scaffold and/or cells for growth and/or for other procedures or manipulations. In some embodiments, the chamber is configured for monitoring and/or modulating the growth conditions within the chamber. In some embodiments, the chamber is configured for directly monitoring the conditions of the cells or substitute tissue or organ within the chamber, or for monitoring the conditions of the chamber itself, or for a combination thereof. In some embodiments, one or more techniques for monitoring fluid or gas flow in a chamber and/or within an engineered tissue or organ within the chamber may be used. For example, in some embodiments, IR levels or patterns as a function of time are used to detect and/or evaluate fluid or gas flow (e.g., by comparing them to known IR levels or patterns indicative of acceptable flow levels or to known reference levels or patterns that are indicative of insufficient or excessive flow levels). In some embodiments, one or more pulses of fluid or gas at a detectable temperature (e.g., at a temperature that is different—either higher or lower—than the gas and/or fluid being used in the bioreactor are introduced into the bioreactor and/or engineered tissue or organ. By following the pulse of fluid or gas, the flow pattern and/or rate can be determined or evaluated within the bioreactor and/or engineered tissue or organ. In some embodiments, the rate of flow in the bioreactor can be adjusted if the rate that is calculated based on flow of the gas or fluid pulse is too low or too high.

A bioreactor can include one or more inlet and/or outlet ports that can be adjusted based on fluid or gas flow rates determined as described herein. In some embodiments, fluid or gas flow rates are evaluated within tubes or conduits connected to one or more bioreactor inlets or outlet. In some embodiments, fluid or gas flow patterns within a chamber of a bioreactor can be evaluated as described herein (e.g., using a pulse of gas or liquid at a different temperature). In some embodiments, depending on the size of the chamber, different reference patterns may be used (e.g., a reference pattern indicative of a desirable flow pattern can be used in some embodiments, or a reference pattern indicative of an undesirable flow pattern can be used other embodiments). It should be appreciated that a bioreactor chamber may have any suitable size for containing a liquid, a gas, a scaffold, or other entity. For example, the chamber may have a volume from about 0.1 L and about 0.5 L, about 0.1 L and about 1 L, about 1 L and about 5 L, and from about 1 L and about 10 L. Larger volumes are also possible (e.g., 10-20 L, 20-30 L, 30-40 L, 40-50 L, or larger). The volumes may depend on the particular use of the bioreactor (e.g., the size of the scaffold, the particular tissue or organ being grown, etc.).

Having thus described several embodiments with respect to aspects of the inventions, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Methods described herein can be used to evaluate structural properties of a scaffold that includes any combination of synthetic material, a bioreactor or a component thereof, or a combination thereof (e.g., a scaffold attached to a bioreactor). In some embodiments, an infrared level or pattern is obtained and evaluated. In some embodiments, an infrared signal is obtained at a constant temperature. In some embodiments, an infrared signal in response to a change in temperature is obtained. In some embodiments, the scaffold is exposed to a first temperature and then a second temperature. The change in IR emissivity during the transition from the first to the second temperature can be evaluated. In some embodiments, a synthetic scaffold can be coated in a solution (e.g., an aqueous solution) and the change in IR emissivity as the solution is absorbed and/or evaporates can be detected an evaluated. In some embodiments, an infrared signal in response to a perfusion (e.g., of one or more channels within the scaffold) is obtained. In some embodiments, an infrared signal in response to one or more physical or chemical challenges is obtained. For example, an infrared signal may be obtained for a synthetic scaffold during or after a physical challenge (e.g., during or after stretching, compression, twisting, or any combination thereof). In some embodiments, an infrared signal can be evaluated to determine whether it is indicative or desirable or undesirable physical or functional properties. For example, in some embodiments, the extent of liquid or gas flow through one or more perfusion channels within a synthetic scaffold can be evaluated (e.g., to determine whether fluid or gas is reaching all the intended portions of the scaffold). In some embodiments, the presence of an unwanted leak or tear or other physical abnormality can be detected based on the presence of an abnormal IR signal (e.g., for a portion of a synthetic scaffold). In some embodiments, an infrared pattern is compared to a reference pattern indicative of a useful scaffold (or bioreactor, bioreactor component, or scaffold attached to a bioreactor) or to a different pattern indicative of a defective scaffold (or bioreactor, bioreactor component, or scaffold attached to a bioreactor).

The invention claimed is:

1. A method of detecting a physical or functional property of a biological object, the method comprising:
   detecting a first infrared emission from a first site of the biological object,
   identifying a contrast between the first infrared emission and a second infrared emission, wherein the contrast is indicative of the physical or functional property, and wherein the first infrared emission is detected while the biological object is present in a subject.

2. The method of claim 1, wherein the biological object is an engineered tissue or organ.

3. The method of claim 2, wherein the engineered tissue or organ comprises a synthetic scaffold.

4. The method of claim 2, wherein the physical or functional property is an extent of fluid perfusion through the engineered tissue or organ.

5. The method of claim 4, wherein the fluid comprises cells, molecules, growth factors, nutrients, or waste.

6. The method of claim 4, wherein the fluid is perfused through one or more conduits within the engineered tissue or organ.

7. The method of claim 2, wherein the physical or functional property is an extent of cellularization of the engineered tissue or organ.

8. The method of claim 1, wherein the biological object is a tissue or organ, and wherein the physical or functional property is an extent of injury, disease, damage, or growth of the tissue or organ.

9. The method of claim 1, wherein the first infrared emission is detected from the first site of the biological object using an infrared camera.

10. A method of detecting a physical or functional property of a biological object, the method comprising:
    detecting a first infrared emission from a first site of the biological object,
    identifying a contrast between the first infrared emission and a second infrared emission, wherein the contrast is indicative of the physical or functional property, and wherein the first infrared emission is detected while the biological object is present in a bioreactor.

11. The method of claim 10, wherein the biological object is a tissue or organ.

12. The method of claim 11, wherein the biological object is skin, lung, liver, heart, muscle, airway, or kidney.

13. The method of claim 11, wherein the physical or functional property is an extent of injury, disease, damage, or growth of the tissue or organ.

14. The method of claim 11, wherein the first site comprises at least a portion of a conduit of the tissue or organ.

15. The method of claim 14, wherein the conduit is a branched conduit.

16. The method of claim 11, wherein the physical or functional property is an extent of hydration or vascularization of the tissue or organ.

17. The method of claim 10, wherein the second infrared emission is a reference level of infrared emission.

18. The method of claim 11, wherein the tissue or organ is engineered.

19. The method of claim 18, wherein the tissue or organ comprises a synthetic scaffold.

20. The method of claim 18, wherein the physical or functional property is an extent of fluid perfusion through the engineered-tissue or organ.

21. The method of claim 20, wherein the fluid comprises cells, molecules, growth factors, nutrients, or waste.

22. The method of claim 20, wherein the fluid is perfused through one or more conduits within the engineered tissue or organ.

23. The method of claim 18, wherein the physical or functional property is an extent of cellularization of the engineered tissue or organ.

24. The method of claim 10, wherein the first infrared emission is detected from the first site of the biological object using an infrared camera.

25. A method of detecting a physical or functional property of an engineered tissue or organ, the method comprising:
    detecting a first infrared emission from a first site of the engineered tissue or organ,
    identifying a contrast between the first infrared emission and a second infrared emission, wherein the contrast is indicative of a physical or functional property, and wherein the first site comprises at least a portion of a conduit of the engineered tissue or organ.

26. The method of claim 25, wherein the conduit is a branched conduit.

27. The method of claim 25, wherein the engineered tissue or organ comprises a synthetic scaffold.

28. The method of claim 25, wherein the physical or functional property is an extent of fluid perfusion through the engineered tissue or organ.

29. The method of claim 28, wherein the fluid comprises cells, molecules, growth factors, nutrients, or waste.

30. The method of claim 28, wherein the fluid is perfused through one or more conduits within the engineered tissue or organ.

31. The method of claim 25, wherein the first infrared emission is detected from the first site of engineered tissue or organ using an infrared camera.

32. A method of detecting a physical or functional property of an engineered tissue or organ, the method comprising:
    detecting a first infrared emission from a first site of the engineered tissue or organ,
    identifying a contrast between the first infrared emission and a second infrared emission, wherein the contrast is indicative of a physical or functional property, and wherein the physical or functional property is an extent of hydration or vascularization of the engineered tissue or organ.

33. The method of claim 32, wherein the engineered tissue or organ comprises a synthetic scaffold.

34. The method of claim 32, wherein the physical or functional property is an extent of hydration of the engineered tissue or organ, and wherein the first infrared emission is detected from the first site of the engineered tissue or organ using an infrared camera.

35. The method of claim 32, wherein the physical or functional property is an extent of vascularization of the engineered tissue or organ, and wherein the first infrared emission is detected from the first site of the engineered tissue or organ using an infrared camera.

* * * * *